(12) United States Patent
Boday et al.

(10) Patent No.: US 11,067,568 B2
(45) Date of Patent: *Jul. 20, 2021

(54) TRENCHED SAMPLE ASSEMBLY FOR DETECTION OF ANALYTES WITH ELECTROMAGNETIC READ-WRITE HEADS

(71) Applicant: International Business Machines Corporation, Armonk, NY (US)

(72) Inventors: Dylan J. Boday, Tucson, AZ (US); Stephen L. Schwartz, Tucson, AZ (US); Anna W. Topol, Clifton Park, NY (US); Sandra L. Waters, Austin, TX (US); Daniel J. Winarski, Tucson, AZ (US)

(73) Assignee: International Business Machines Corporation, Armonk, NY (US)

( * ) Notice: Subject to any disclaimer, the term of this patent is extended or adjusted under 35 U.S.C. 154(b) by 947 days.

This patent is subject to a terminal disclaimer.

(21) Appl. No.: 15/096,175

(22) Filed: Apr. 11, 2016

(65) Prior Publication Data

US 2016/0223533 A1 Aug. 4, 2016

Related U.S. Application Data

(60) Continuation of application No. 14/869,734, filed on Sep. 29, 2015, now Pat. No. 10,317,398, which is a
(Continued)

(51) Int. Cl.
*G01N 33/543* (2006.01)
*G01N 27/74* (2006.01)
*B82Y 15/00* (2011.01)

(52) U.S. Cl.
CPC ..... *G01N 33/54333* (2013.01); *G01N 27/745* (2013.01); *G01N 33/54346* (2013.01);
(Continued)

(58) Field of Classification Search
CPC .... B82Y 15/00; G01N 27/745; G01N 33/543; G01N 33/54333; G01N 33/54346; G01N 33/54366
(Continued)

(56) References Cited

U.S. PATENT DOCUMENTS

| 2,376,965 A | 5/1945 | Otto |
| 2,948,624 A | 8/1960 | Watson et al. |

(Continued)

FOREIGN PATENT DOCUMENTS

| CN | 1454851 A | 11/2003 |
| CN | 1783219 A | 6/2006 |

(Continued)

OTHER PUBLICATIONS https://en.wikipedia.org/wiki/Thermoelectric_cooling (Year: 2019) The Office notes that the Peltier Effect was discovered by J. Peltier prior to 1845.*

(Continued)

*Primary Examiner* — Christopher L Chin
*Assistant Examiner* — Richard Moerschell
(74) *Attorney, Agent, or Firm* — Zilka-Kotab, P.C.

(57) ABSTRACT

Described are embodiments of an invention for detecting target antigens in a biological sample using a sample assembly. Detection may be accomplished by performing a method comprising: sweeping a head module over the sample assembly, wherein said head module includes at least one magneto-resistive read sensor configured to detect target antigens via nanoparticles within the sample assembly; and detecting at least one particular antigen among the target antigens. Preferably, detecting the target antigens via the nanoparticles is based at least in part on detecting unique magnetic properties of particular nanoparticles specifically associated with different types of the target antigens. Detec-
(Continued)

tion using a magnetic read/write head in the sample assembly facilitates automation of sample detection with high speed and fidelity. Corresponding systems are also disclosed.

5 Claims, 7 Drawing Sheets

Related U.S. Application Data division of application No. 12/970,837, filed on Dec. 16, 2010, now Pat. No. 9,304,130.

(52) U.S. Cl.
CPC ........ *G01N 33/54366* (2013.01); *B82Y 15/00* (2013.01); *G01N 33/543* (2013.01)

(58) Field of Classification Search
USPC ........................................ 436/518
See application file for complete search history.

(56) References Cited

U.S. PATENT DOCUMENTS

| | | | |
|---|---|---|---|
| 3,823,276 A | 7/1974 | Maslowski et al. | |
| 4,062,047 A | 12/1977 | Scull | |
| 4,292,920 A | 10/1981 | Smith et al. | |
| 4,708,931 A * | 11/1987 | Christian | B01J 19/0093 422/503 |
| 5,005,096 A | 4/1991 | Krounbi et al. | |
| 5,146,004 A | 9/1992 | Morris et al. | |
| 5,189,571 A | 2/1993 | Murphy et al. | |
| 5,206,159 A | 4/1993 | Cohen et al. | |
| 5,206,590 A | 4/1993 | Dieny et al. | |
| 5,331,493 A | 7/1994 | Schwarz | |
| 5,376,965 A | 12/1994 | Nagasaki et al. | |
| 5,452,164 A | 9/1995 | Cole et al. | |
| 5,465,185 A | 11/1995 | Heim et al. | |
| 5,615,065 A | 3/1997 | Cheung | |
| 5,661,039 A | 8/1997 | Kung et al. | |
| 5,689,384 A | 11/1997 | Albrecht et al. | |
| 5,689,394 A | 11/1997 | Esser et al. | |
| 5,736,349 A | 4/1998 | Sasaki et al. | |
| 5,764,567 A | 6/1998 | Parkin | |
| 5,840,889 A | 11/1998 | Cavalieri et al. | |
| 5,863,507 A | 1/1999 | James | |
| 5,922,537 A | 7/1999 | Ewart et al. | |
| 5,948,624 A | 9/1999 | Rothschild et al. | |
| 5,965,375 A * | 10/1999 | Valkirs | C12Q 1/32 435/26 |
| 6,013,531 A | 1/2000 | Wang et al. | |
| 6,021,013 A | 2/2000 | Albrecht et al. | |
| 6,027,946 A | 2/2000 | Weitschies et al. | |
| 6,282,051 B1 | 8/2001 | Albrecht et al. | |
| 6,320,719 B1 | 11/2001 | Albrecht et al. | |
| 6,432,346 B1 | 8/2002 | Hall | |
| 6,462,904 B1 | 10/2002 | Albrecht et al. | |
| 6,493,172 B1 | 12/2002 | Morris et al. | |
| 6,548,311 B1 | 4/2003 | Knoll | |
| 6,643,084 B1 | 11/2003 | Andrew et al. | |
| 6,736,978 B1 | 5/2004 | Porter et al. | |
| 6,770,489 B1 | 8/2004 | Enpuku | |
| 6,962,685 B2 | 11/2005 | Sun | |
| 7,153,366 B1 | 12/2006 | Chen et al. | |
| 7,342,738 B1 | 3/2008 | Anderson et al. | |
| 7,556,863 B2 | 7/2009 | Beming et al. | |
| 7,639,448 B2 | 12/2009 | Haustein et al. | |
| 7,639,488 B2 | 12/2009 | Tu | |
| 7,649,708 B2 | 1/2010 | Winarski et al. | |
| 7,649,709 B2 | 1/2010 | Winarski et al. | |
| 7,679,858 B2 | 3/2010 | Winarski et al. | |
| 7,960,184 B2 | 6/2011 | Morozov et al. | |
| 8,694,280 B2 | 4/2014 | Awezec et al. | |
| 9,034,660 B2 * | 5/2015 | Boday | B82Y 15/00 422/50 |
| 9,081,004 B2 | 7/2015 | Boday et al. | |
| 9,304,130 B2 * | 4/2016 | Boday | G01N 33/54333 |
| 9,435,800 B2 * | 9/2016 | Bates | G01N 33/54326 |
| 10,132,804 B2 | 11/2018 | Bates et al. | |
| 10,317,398 B2 | 6/2019 | Boday et al. | |
| 10,393,737 B2 | 8/2019 | Bates et al. | |
| 2002/0001960 A1 | 1/2002 | Wu et al. | |
| 2002/0030044 A1 | 3/2002 | Brown | |
| 2002/0119470 A1 | 8/2002 | Nerenberg et al. | |
| 2002/0174453 A1 | 11/2002 | Daniell et al. | |
| 2003/0077616 A1 | 4/2003 | Lomas | |
| 2003/0077642 A1 | 4/2003 | Fritsch et al. | |
| 2003/0186465 A1 | 10/2003 | Kraus et al. | |
| 2004/0002125 A1 | 1/2004 | Gombrich et al. | |
| 2004/0061968 A1 | 4/2004 | Fukushima et al. | |
| 2004/0080855 A1 | 4/2004 | Tsuchiya et al. | |
| 2004/0132220 A1 | 7/2004 | Fish | |
| 2004/0166508 A1 | 8/2004 | Pawlak et al. | |
| 2004/0219361 A1 | 11/2004 | Cui et al. | |
| 2004/0219631 A1 | 11/2004 | Yokozeki et al. | |
| 2005/0087000 A1 | 4/2005 | Coehoorn et al. | |
| 2005/0100930 A1 | 5/2005 | Wang et al. | |
| 2006/0020371 A1 | 1/2006 | Ham et al. | |
| 2006/0040273 A1 | 2/2006 | Chaiken et al. | |
| 2006/0051237 A1 | 3/2006 | Wang et al. | |
| 2006/0128035 A1 | 6/2006 | Coehoorn et al. | |
| 2006/0216696 A1 | 9/2006 | Goguen | |
| 2007/0054154 A1 | 3/2007 | Leu | |
| 2007/0115578 A1 | 5/2007 | Winarski et al. | |
| 2007/0117151 A1 * | 5/2007 | Frederix | G01N 21/554 435/7.1 |
| 2007/0146715 A1 | 6/2007 | Potyrailo et al. | |
| 2007/0146925 A1 | 6/2007 | Haustein et al. | |
| 2008/0012119 A1 | 1/2008 | Otremba et al. | |
| 2008/0036450 A1 | 2/2008 | Kahlman et al. | |
| 2008/0206104 A1 | 8/2008 | Prins et al. | |
| 2008/0226917 A1 | 9/2008 | Zhong et al. | |
| 2009/0021856 A1 | 1/2009 | Winarski et al. | |
| 2009/0027801 A1 | 1/2009 | Winarski et al. | |
| 2009/0042317 A1 | 2/2009 | Ikeda | |
| 2009/0047520 A1 | 2/2009 | Lee et al. | |
| 2009/0066318 A1 | 3/2009 | Kahlman et al. | |
| 2009/0072815 A1 | 3/2009 | Kahlman et al. | |
| 2009/0104707 A1 | 4/2009 | Wang et al. | |
| 2009/0152657 A1 | 6/2009 | Suh et al. | |
| 2009/0170212 A1 | 7/2009 | Van Der Wijk et al. | |
| 2009/0212768 A1 | 8/2009 | Llandro et al. | |
| 2009/0243594 A1 | 10/2009 | Kahlman | |
| 2009/0268325 A1 | 10/2009 | Iben et al. | |
| 2009/0273857 A1 | 11/2009 | Iben et al. | |
| 2009/0314066 A1 | 12/2009 | Nieuwenhuis et al. | |
| 2010/0017922 A1 | 1/2010 | Shin et al. | |
| 2010/0021708 A1 | 1/2010 | Kong et al. | |
| 2010/0065427 A1 * | 3/2010 | Fujita | B01L 3/502715 204/451 |
| 2010/0093119 A1 | 4/2010 | Shimizu | |
| 2010/0147003 A1 | 6/2010 | Ueda et al. | |
| 2011/0053289 A1 | 3/2011 | Lowe et al. | |
| 2011/0070440 A1 | 3/2011 | Linhardt et al. | |
| 2011/0076670 A1 | 3/2011 | Boday et al. | |
| 2011/0076726 A1 | 3/2011 | Lakey et al. | |
| 2011/0076782 A1 | 3/2011 | Awezec et al. | |
| 2011/0077869 A1 | 3/2011 | Boday et al. | |
| 2011/0077902 A1 | 3/2011 | Awezec et al. | |
| 2011/0262955 A1 | 10/2011 | Licher et al. | |
| 2011/0293940 A1 | 12/2011 | Tokoro et al. | |
| 2012/0157330 A1 | 6/2012 | Boday et al. | |
| 2012/0164717 A1 | 6/2012 | Irudayaraj | |
| 2012/0280675 A1 | 11/2012 | Berman et al. | |
| 2012/0283976 A1 | 11/2012 | Berman et al. | |
| 2014/0080118 A1 | 3/2014 | Bates et al. | |
| 2016/0018392 A1 | 1/2016 | Boday et al. | |
| 2016/0274099 A1 | 9/2016 | Bates et al. | |
| 2016/0274102 A1 | 9/2016 | Bates et al. | |

FOREIGN PATENT DOCUMENTS

| | | |
|---|---|---|
| CN | 1967660 A | 5/2007 |
| CN | 101509919 A | 8/2009 |

(56) References Cited

FOREIGN PATENT DOCUMENTS

| CN | 101558313 A | 10/2009 |
|---|---|---|
| CN | 101632018 A | 1/2010 |
| EP | 2073016 A1 | 6/2009 |
| WO | 2005010542 A2 | 2/2005 |
| WO | 2006047840 A1 | 5/2006 |
| WO | 2006079998 A1 | 8/2006 |
| WO | 2007114512 A1 | 10/2007 |
| WO | 2008102218 A1 | 8/2008 |
| WO | 2009039437 A1 | 3/2009 |
| WO | 2009083856 A2 | 7/2009 |
| WO | 2009157739 A2 | 12/2009 |

OTHER PUBLICATIONS

Supplemental Notice of Allowance from U.S. Appl. No. 15/169,479, dated Aug. 15, 2018.
Final Office Action from U.S. Appl. No. 14/869,734, dated Sep. 27, 2018.
Notice of Allowance from U.S. Appl. No. 15/169,479, dated Jul. 12, 2018.
Non-Final Office Action from U.S. Appl. No. 15/169,340, dated Jul. 27, 2018.
Supplemental Notice of Allowance from U.S. Appl. No. 13/616,855, dated Apr. 19, 2016.
Bates et al., U.S. Appl. No. 15/169,340, filed May 31, 2016.
Bates et al., U.S. Appl. No. 15/169,479, filed May, 31, 2016.
Awezec et al., U.S. Appl. No. 61/246,329, filed Sep. 28, 2009.
Final Office Action from U.S. Appl. No. 13/099,360, dated Feb. 25, 2014.
Non-Final Office Action from U.S. Appl. No. 13/099,360, dated Oct. 1, 2013.
Notice of Allowance from U.S. Appl. No. 13/099,358, dated Sep. 15, 2014.
Notice of Allowance from U.S. Appl. No. 13/099,360, dated Jun. 4, 2014.
Restriction Requirement from U.S. Appl. No. 13/099,358, dated Jun. 20, 2014.
Advisory Action from U.S. Appl. No. 12/888,388, dated Jul. 25, 2013.
Final Office Action from U.S. Appl. No. 12/888,388, dated May 9, 2013.
Notice of Allowance from U.S. Appl. No. 12/888,388, dated Jan. 12, 2015.
Non-Final Office Action from U.S. Appl. No. 12/888,388, dated Jan. 7, 2013.
Restriction Requirement from U.S. Appl. No. 12/888,388, dated Aug. 28, 2012.
Non-Final Office Action from U.S. Appl. No. 12/888,394, dated Oct. 7, 2013.
Restriction Requirement from U.S. Appl. No. 12/888,394, dated Dec. 10, 2012.
Final Office Action from U.S. Appl. No. 12/888,403, dated Feb. 21, 2013.
Notice of Allowance from U.S. Appl. No. 12/888,403, dated Nov. 22, 2013.
Non-Final Office Action from U.S. Appl. No. 12/888,403, dated Jun. 14, 2013.
Non-Final Office Action from U.S. Appl. No. 12/888,403, dated Sep. 20, 2012.
Advisory Action from U.S. Appl. No. 12/888,408, dated Feb. 26, 2015.
Final Office Action from U.S. Appl. No. 12/888,408, dated Dec. 10, 2014.
Non-Final Office Action from U.S. Appl. No. 12/888,408 dated May 23, 2014.
Non-Final Office Action from U.S. Appl. No. 14/869,734, dated Jun. 6, 2018.
Non-Final Office Action from U.S. Appl. No. 15/169,479, dated Jan. 18, 2018.
Boday et al., U.S. Appl. No. 12/970,837, filed Dec. 16, 2010.
Restriction Requirement from U.S. Appl. No. 12/970,837, dated Jan. 29, 2013.
Non-Final Office Action from U.S. Appl. No. 12/970,837, dated May 10, 2013.
Final Office Action from U.S. Appl. No. 12/970,837, dated Nov. 22, 2013.
Notice of Allowance from U.S. Appl. No. 12/970,837, dated Jan. 8, 2015.
Bates et al., U.S. Appl. No. 13/616,855, filed Sep. 14, 2012.
Non-Final Office Action from U.S. Appl. No. 13/616,855, dated Jun. 4, 2013.
Non-Final Office Action from U.S. Appl. No. 13/616,855, dated Dec. 30, 2013.
Final Office Action from U.S. Appl. No. 13/616,855, dated Jul. 24, 2014.
Office Action from German Application No. 112011104401.1, dated May 13, 2015.
Chinese Office Action from Application No. 201180060053.7 dated Jun. 27, 2014.
International Search Report and Written Opinion from International Application No. PCT/EP2011/070578, dated Mar. 19, 2012.
Awezec et al., U.S. Appl. No. 12/888,394, filed Sep. 22, 2010.
Awezec et al., U.S. Appl. No. 12/888,403, filed Sep. 22, 2010.
Boday et al., U.S. Appl. No. 12/888,408, filed Sep. 22, 2010.
Boday et al., U.S. Appl. No. 12/888,388, filed Sep. 22, 2010.
Crowther, J., "The ELISA Guidebook," Humana Press, Totowa, New Jersey, 2001, pp. 1-425.
Fox et al., "Tear and Serum Antibody Levels in Ocular Herpetic Infection: Diagnostic Precision of Secretory IgA," British Journal of Ophthalmology, vol. 70, 1986, pp. 584-588.
Liu et al., "Discrimination of specific and non-specific bindings by dielectrophoretic repulsion in on-chip magnetic bio-assays," Journal of Biosensors and Bioelectronics, No. 24, 2009, pp. 2294-2297.
Llandro et al., "Magnetic biosensor technologies for medical applications: a review," Med. and Biol. Eng. And Computing, Springer Berlin, Jun. 15, 2010, 22 Pages.
Millen et al., "Giant Magenetoresistive Sensors. 2. Detection of Biorecognition Events at Self-Referencing and Magnetically Tagged Arrays", Analytical Chemistry, vol. 80, No. 21, pp. 7940-7946, Nov. 1, 2008.
Nordling et al., "Giant Magnetoresistance Sensors. 1. Internally Calibrated Readout of Scanned Magnetic Arrays," Anal. Chem., vol. 80, 2008, pp. 7930-7939.
Osterfeld et al., "Multiplex protein assays based on real-time magnetic nanotag sensing," PNAS, vol. 105, No. 52. Dec. 30, 2008, pp. 20637-20640.
Piedade et al., "A New Hand-Held Microsystem Architecture for Biological Analysis," IEEE Trans. on Circuits and Systems—I: Regular Papers, vol. 53, No. 11, Nov. 2006, pp. 2384-2395.
Schuurs et al., "Enzyme—Immunoassay," Clini Chim Acta, vol. 81, 1977, pp. 1-40.
Shen et al., "Detection of DNA labeled with magnetic nanoparticles using MgO-based magnetic tunnel junction sensors," Journal of Applied Physics, vol. 103, 2008, pp. 07 A306-1-07 A306-3.
Yammamoto et al., "Active immobilization of biomolecules on a hybrid three-dimensional nanoelectrode by dielectrophoresis for single-biomolecule study," Nanotechnology, vol. 18,2007,495503, pp. 1-7.
Statement of Relevance of Non-Translated Foreign Document WO2009157739.
Boday et al., U.S. Appl. No. 14/869,734, filed Sep. 29, 2015.
Non-Final Office Action from U.S. Appl. No. 13/616,855, dated Nov. 20, 2015.
Notice of Allowance from U.S. Appl No. 12/970,837, dated Jan. 7, 2016.
Supplemental Notice of Allowance from U.S. Appl. No. 12/970,837, dated Mar. 1, 2016.
Notice of Allowance from U.S. Appl. No. 13/616,855, dated Mar. 15, 2016.
Supplemental Notice of Allowance from U.S. Appl. No. 15/169,340, dated Jun. 14, 2019.

(56) References Cited

OTHER PUBLICATIONS

Notice of Allowance from U.S. Appl. No. 15/169,340, dated Apr. 18, 2019.
Notice of Allowance from U.S. Appl. No. 14/869,734, dated Jan. 30, 2019.
Final Office Action from U.S. Appl. No. 15/169,340, dated Feb. 7, 2019.
Supplemental Notice of Allowance from U.S. Appl. No. 14/869,734, dated Mar. 20, 2019.
Corrected Notice of Allowance from U.S. Appl. No. 14/869,734, dated Apr. 30, 2019.
Notice of Allowance from U.S. Appl. No. 14/869,734, dated Dec. 17, 2018.
Examination Report from European Application No. GB1312478.9, dated Nov. 28, 2018.
Supplemental Notice of Allowance from U.S. Appl. No. 15/169,340, dated Jul. 31, 2019.

* cited by examiner

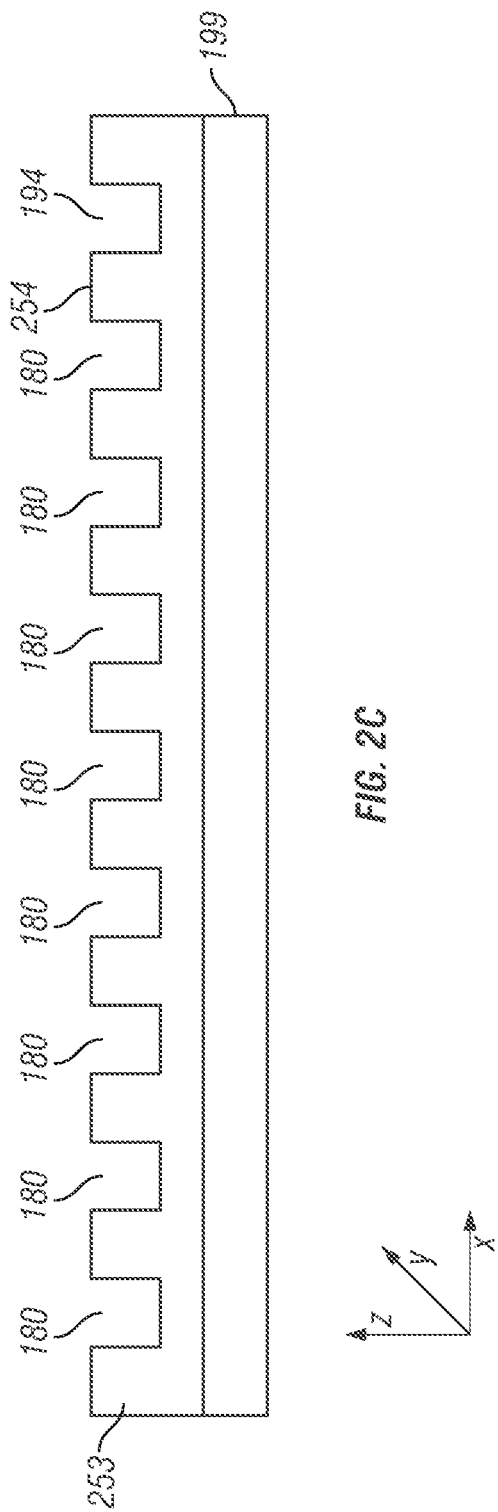

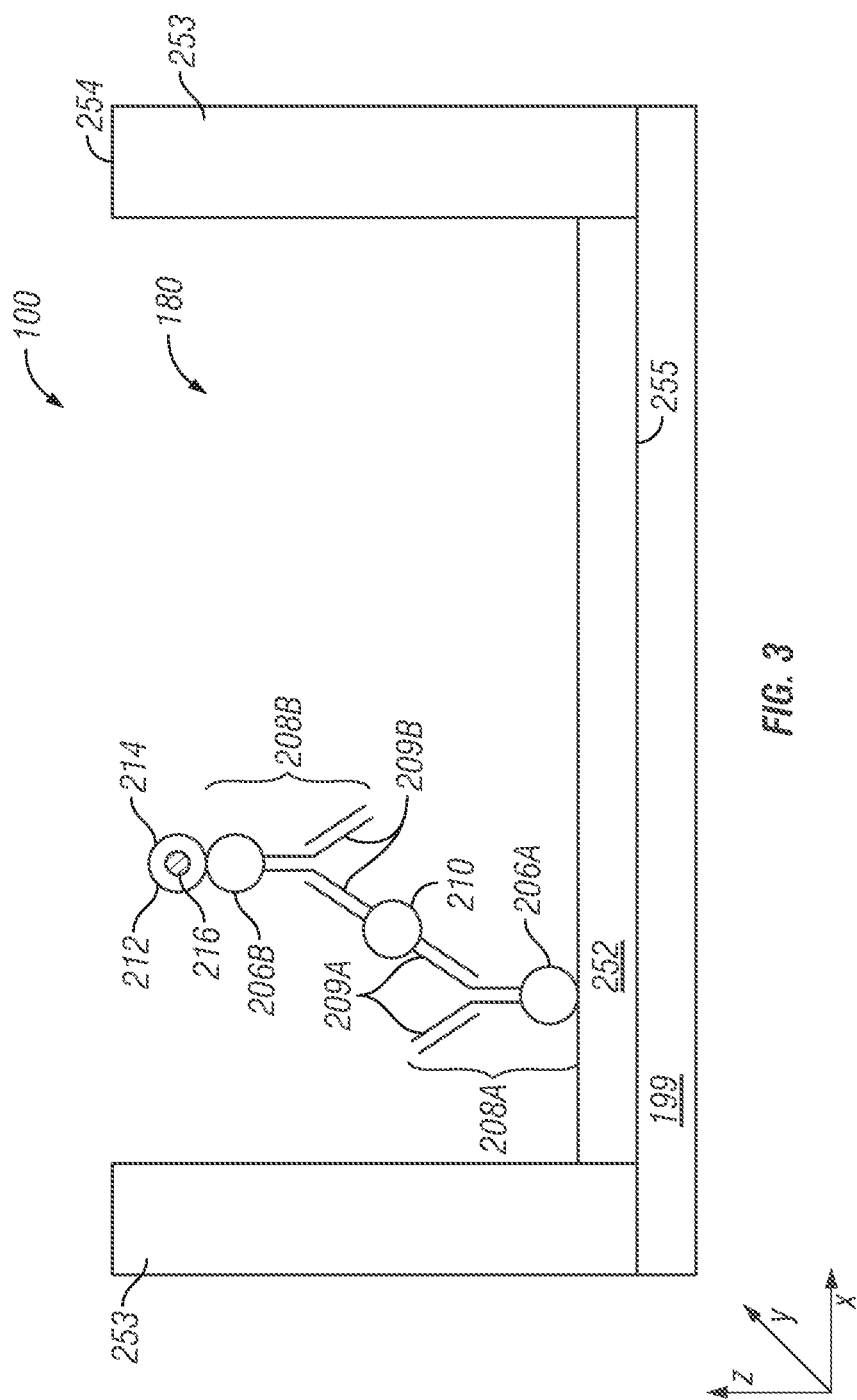

TRENCHED SAMPLE ASSEMBLY FOR DETECTION OF ANALYTES WITH ELECTROMAGNETIC READ-WRITE HEADS

RELATED APPLICATIONS

This application is a continuation of U.S. application Ser. No. 14/869,734, filed Sep. 29, 2015, which is a divisional of U.S. application Ser. No. 12/970,837, filed Dec. 16, 2010, the entire contents of which are incorporated herein by reference. These applications are related to cofiled, copending and coassigned U.S. patent application Ser. No. 12/888,388 entitled "DETECTION OF ANALYTES VIA NANOPARTICLE-LABELED SUBSTANCES WITH ELECTROMAGNETIC READ-WRITE HEADS", Ser. No. 12/888,394 entitled "READ-AFTER-WRITE DETECTION OF ANALYTES VIA NANOPARTICLE-LABELED SUBSTANCES", U.S. patent application Ser. No. 12/888,403 entitled "A SERVO CONTROL CIRCUIT FOR DETECTING ANALYTES VIA NANOPARTICLE-LABELED SUBSTANCES WITH ELECTROMAGNETIC READ-WRITE HEADS", and U.S. patent application Ser. No. 12/888,408 entitled "A CIRCUIT FOR DETECTING ANALYTES VIA NANOPARTICLE-LABELED SUBSTANCES WITH ELECTROMAGNETIC READ-WRITE HEADS," all of which were filed on Sep. 22, 2010 and are hereby incorporated by reference.

BACKGROUND

The present invention relates to analytical devices and processes, and more particularly, to devices and processes that incorporate electromagnetic write-heads and magneto-resistive read-sensors to detect target antigens.

It is known that antibodies bind with antigens as part of the human disease defense system. Presently, antigens are detected by such techniques as immunofluorescence, immunoperoxidase, or enzyme-linked immunosorbent assay (ELISA), each of which then employs a microscope for visual detection of the target antigen. It is desirable to exploit the use of magnetic signaling technology to automate the detection of analytes, such as antigens, and to further apply this technology to the detection of any biological matter.

SUMMARY

Described are embodiments for detecting target antigens in a biological sample using a sample assembly. Detection may be accomplished by performing a method comprising: sweeping a head module over the sample assembly, wherein said head module includes at least one magneto-resistive read sensor configured to detect target antigens via nanoparticles within the sample assembly; and detecting at least one particular antigen among the target antigens.

The detection may be accomplished, in various embodiments, using a head module as noted above in conjunction with a sample assembly, the sample assembly comprising: a substrate; a base layer formed above a substrate; an outer layer formed above the base layer; at least one sample trench formed in the outer layer; and a plurality of servo alignment marks formed in proximity to one or more of the at least one sample trench.

For a fuller understanding of the present invention, reference should be made to the following detailed description taken in conjunction with the accompanying drawings.

BRIEF DESCRIPTION OF THE DRAWINGS

FIG. 2C is a cross-sectional view of sample assembly, not drawn to scale, including sample trenches and an alignment trench in accordance with an embodiment of the invention;

FIG. 3 is a cross-sectional view of a portion of a sample assembly, not drawn to scale, including a biological sample in accordance with an embodiment of the invention;

DETAILED DESCRIPTION

The present invention is described in exemplary embodiments in the following description with reference to the Figures, in which like numbers represent the same or similar elements. While the invention is described in terms of the best mode for achieving the invention's objectives, it will be appreciated by those skilled in the art that variations may be accomplished in view of these teachings without deviating from the spirit or scope of the invention.

Described are embodiments of an invention for a sample assembly with trenches for detection of analytes with electromagnetic read heads. The sample assembly includes an outer layer with at least one sample trench. The sample trench includes a first set of antibodies that are bonded on a first surface of a base layer. Target antigens are bonded with the first set of antibodies, and a second set of antibodies are bonded to the target antigens. Further, the sample trench includes nanoparticles that are bonded to the second set of antibodies. A head module includes a write head for magnetizing nanoparticles and a read sensor for detecting the magnetized nanoparticles, and thus, the target antigens. The sample trench constrains the biological sample, and thus the target antigen, during the preparation and subsequent analysis of the biological sample. Accordingly, the target antigen is aligned with read elements of a head module such that the target antigen is reliably and accurately detected. Further, to ensure reliable and accurate detection, the outer layer is formed with a low friction material allowing the read head to remain in contact with the upper surface of the outer layer during the process of detection.

Figure 1:
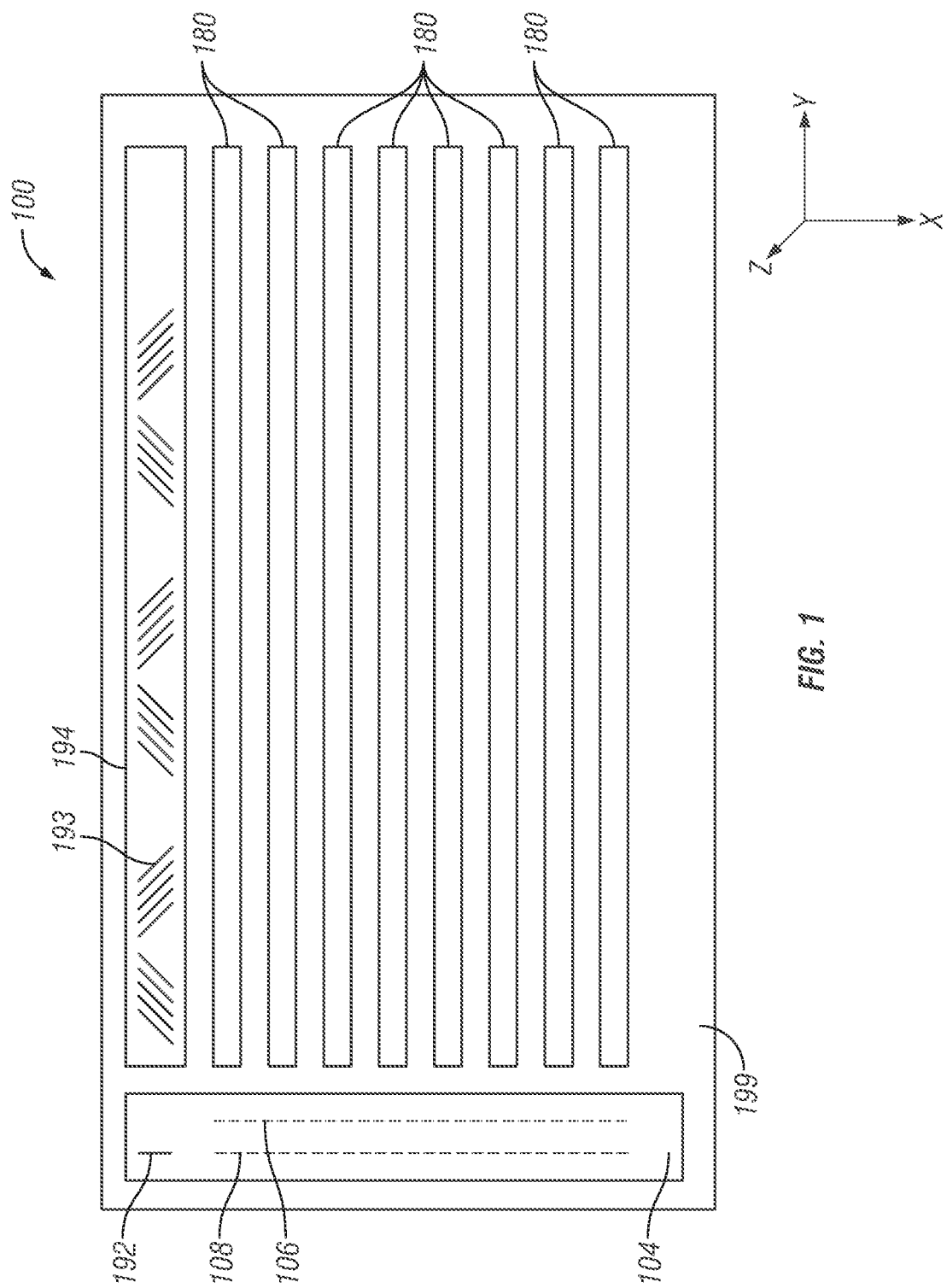
FIG. 1 is a top view of a sample assembly, not drawn to scale, in accordance with an embodiment of the invention.

FIG. 1 is a top view of a sample assembly 100, not drawn to scale, in accordance an embodiment of the invention. The sample assembly 100 includes a substrate 199. The substrate 199 may comprise, without limitations, a Peltier hard-substrate, a glass substrate, a polyethylene terephthalate (PET, which is commonly known by the trade name of Mylar™) substrate, a flexible-substrate, or other materials having similar properties. The term "substrate" refers to any supporting structure, including, but not limited to, the substrates described above. Further, the substrate may include of more than one layer of material.

An outer layer 253 is formed over substrate 199. Deposition techniques utilized herein include, but are not limited to, photolithography, silk-screening, and other similar processes. The outer layer may comprise diamond-like-carbon (DLC), polytetrafluoroethylene, aluminum oxide, polyamides, or other low-friction materials known in the art. The outer layer 253 may be formed to a thickness of between 0.2 to 60 microns. The outer layer 253 includes sample trenches 180. The process of forming the sample trenches 180 is described with respect to FIGS. 2A and 2B.

Figure 2A:
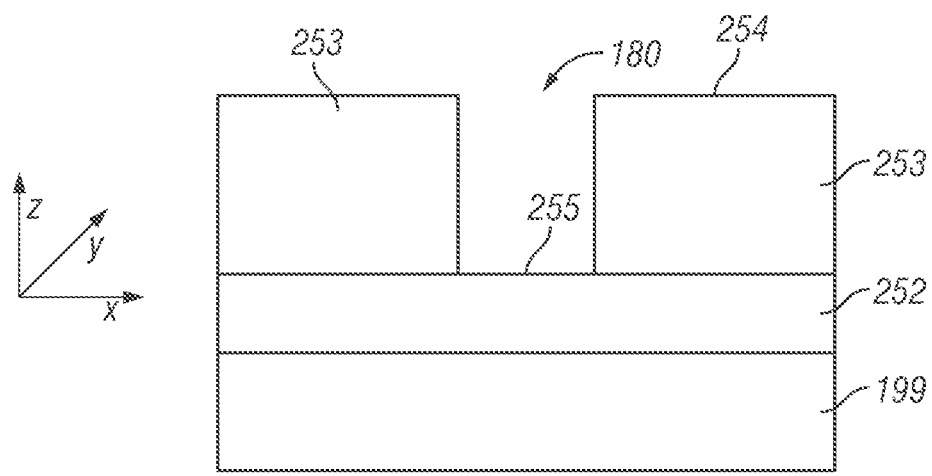
FIG. 2A is a cross-sectional view of a portion of a sample assembly, not drawn to scale, including a sample trench in accordance with an embodiment of the invention.

One embodiment of forming sample trenches 180 is illustrated in FIG. 2A. In this embodiment, a base layer 252 is formed on substrate 199. Base layer 252 may comprise nonmagnetic materials such as gold, silicon, or $SiO_2$, or other materials having similar magnetic properties, without limitation. An outer layer 253 is then formed on base layer 252. Outer layer 253 has an upper surface 254. A plurality of sample trenches 180 are formed within outer layer 253. Sample trenches 180 may be formed by known methods in the art including laser milling, x-ray milling, or photolithographically. Sample trenches 180 may be formed to have a depth of between 0.2 to 60 microns. It should be understood by one of ordinary skill in the art that, while only one sample trench is shown, a plurality of sample trenches 180 may be formed within the outer layer 253 with the same method described herein. Each sample trench 180 is formed having a bottom surface 255. In one embodiment, the bottom surface of the trench exposes base layer 252.

Figure 2B:
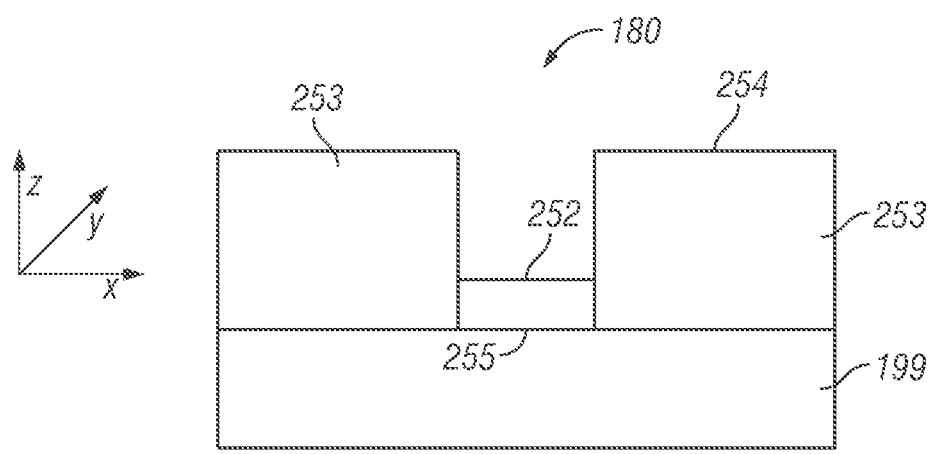
FIG. 2B is a cross-sectional view of a portion of a sample assembly, not drawn to scale, including a sample trench in accordance with another embodiment of the invention.

Another embodiment of forming sample trenches 180 is described with respect to FIG. 2B. In this embodiment, outer layer 253 is formed on substrate 199. The outer layer 253 has an upper surface 254. A plurality of sample trenches 180 are formed within outer layer 253. Sample trenches 180 may be formed by known methods in the art including laser milling, x-ray milling, or photolithographically. Sample trenches may be formed to have a depth of between 0.2 to 60 microns. It should be understood by one of ordinary skill in the art that, while only one sample trench is shown, a plurality of sample trenches 180 may be formed within the outer layer 253 with the same methods described herein. Each sample trench 180 is formed having a bottom surface 255. Base layer 252 is formed within each sample trench 180 and on the bottom surface 255 of each sample trench 180. Base layer 252 may comprise nonmagnetic materials such as gold, silicon, or $SiO_2$, or other materials having similar magnetic properties, without limitations. As shown in FIG. 2B, the base layer 252 only partially fills sample trenches 180. There are many embodiments in which base layer 252 may be formed to only partially fill sample trenches 180. For example, in one embodiment, base layer 252 may be formed conformally over the outer layer 253 and within sample trenches 180. Base layer may then be removed by etching or planarization techniques known in the art. Alternatively, the base layer 252 may be selectively deposited by known methods in the art. The described embodiment of forming a base layer 252 only within the sample trench 180 is particularly advantageous in embodiments in which expensive materials are utilized, such as gold since much less material is required to form the base layer 252.

As shown in FIG. 1, eight sample trenches 180 may be formed to correspond to the head module 104 of the IBM® TS 1130 writing with eight write elements 106 and reading with eight read sensors 108 simultaneously, as further explained below. The sample trenches 180 are parallel to each other and extend along the Y-axis.

In one embodiment, as shown in FIGS. 1 and 2C, the outer layer 253 further includes at least one servo alignment track 194 with a plurality of magnetic servo alignment marks 193. The servo alignment track 194 is parallel with the sample trenches 180 and extends along the Y-axis. The servo alignment track 194 may be a servo alignment trench 194 with a plurality of magnetic servo alignment marks 193. FIG. 2C shows a cross section of substrate 199 along the X-axis illustrating an embodiment in which an alignment trench 194 is formed within outer layer 253. For simplicity of illustration, base layer 252 is not illustrated in FIG. 2C. Alignment trench 194 may be formed in the same manner as described for forming sample trenches 180 shown in FIGS. 2A and 2B. In one embodiment, alignment trench 194 is formed simultaneously with the formation of sample trenches 180. Specifically, alignment trench 194 may be formed by known methods in the art including laser milling, x-ray milling, or photolithographically. Alignment trench 194 may have a depth of between 0.2 to 60 microns. It should be understood by one of ordinary skill in the art that, while only one alignment trench 194 is shown, a plurality of alignment trenches 194 may be formed within the outer layer 253 as described herein. For example, alignment trenches 194 could be formed between each of the sample trenches 180.

In this embodiment, sample trenches 180 are masked and the servo alignment trench 194 is filled with tape ink. The tape ink, which contains magnetic recording particles in a polymer matrix, is cured by methods known in the art. Magnetic encoded servo alignment marks 193 are subsequently encoded in the cured tape ink.

In another embodiment, magnetic encoded servo alignment marks 193 are encoded on a piece of magnetic tape which is adhered to outer layer 253. Further, the magnetic encoded servo alignment marks 193 may be encoded by the manufacturer of substrate 199 on the magnetic tape. Magnetic encoded servo alignment marks 193 may be in the form of timing based servo marks as taught by U.S. Pat. No. 7,639,448 and entitled "Differential Timing Based Servo Pattern for Magnetic-Based Storage Media," which is hereby incorporated by reference in its entirety. Servo alignment marks 193 are read by read sensor 106 and used to keep the write elements 108 and read sensors 106 in alignment with sample trenches 180 along the X-axis while the head module 104 moves relative to sample trenches 180 along the Y-axis.

Still further, in one embodiment the alignment marks 193 may be non-magnetic marks. For example, the alignment marks may be lithographed, silk-screened or ink-jet printed, and read with an optical laser.

The sample trenches 180 include a biological sample having a target antigen. Sample trenches 180 act to constrain the biological sample, and thus the target antigen 210, during the preparation and subsequent analysis of the biological sample, as discussed below. For example, the sample trenches 180 prevent the biological sample from being rinsed away during a rinse step. Further, the sample trenches 180 allow the biological sample and the target antigen to be constrained to an area that is aligned with read elements 108, such that detection of target antigen 210 is reliably and accurately detected.

Figure 4:
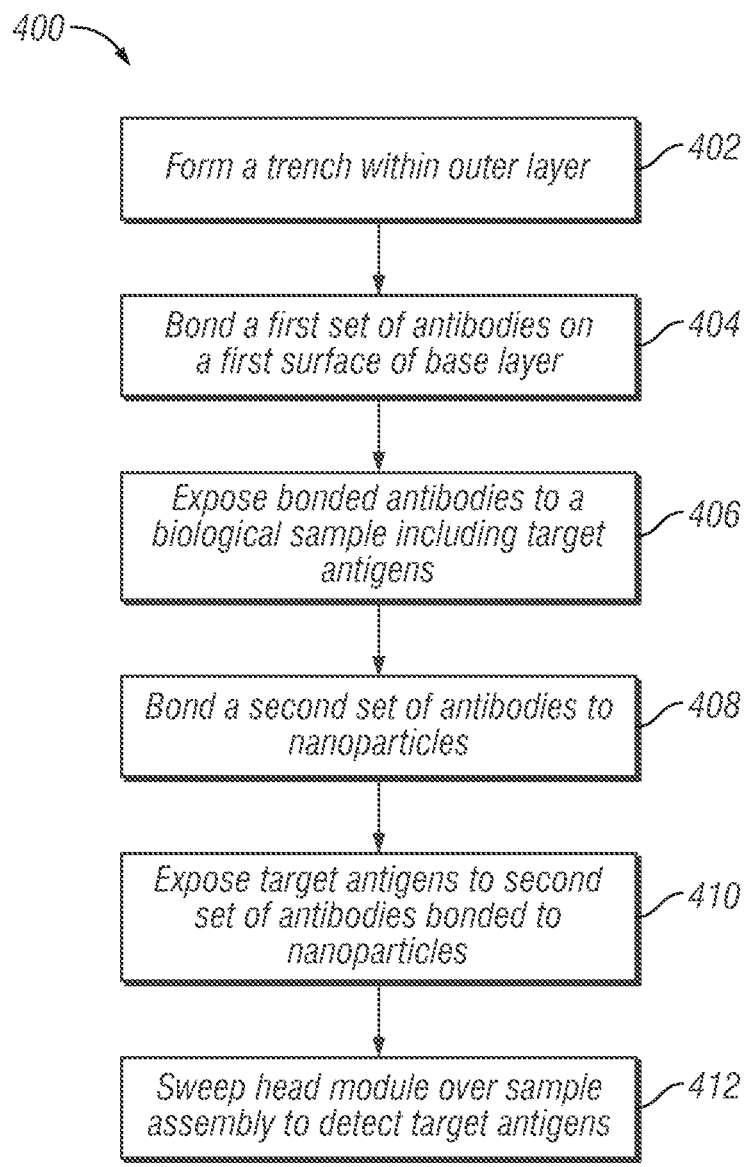
FIG. 4 is a flow chart illustrating steps of an analytic process in accordance with an embodiment of the invention.

The preparation of the biological sample with target antigens 210 within the sample trench 180 is discussed further with respect to FIGS. 3 and 4. FIG. 3 illustrates preparation of biological sample including the target antigen 210 on sample assembly 100. FIG. 4 illustrates the steps of preparing sample assembly 100 and detecting the target antigens 210. For simplicity of explanation, FIG. 3 shows the embodiment in which the base layer 252 is formed within the sample trench 180 and a single sample trench 180. However, it should be understood that the base layer may be formed by any of the methods described herein and a plurality of sample trenches 180 may be formed. As discussed above, an outer layer 253 is formed on substrate 199. In step 402, at least one sample trench 180 is formed in outer layer 253. Base layer 252 is formed on the bottom surface 255 of the sample trench 180.

In step 404, antibodies 208A are bonded within sample trenches 180 to the first surface of base layer 252. The antibodies 208A may be bonded within the sample trenches to the base layer 252 via bonds 206A such as amide, self-assembled-monolayers (SAMS), alkoxysilane, organic functional trialkoxysilane, thiol bonds, or the like. It is important to note that the material of base layer 252 facilitates the bonding of antibody 208A within sample trench 180.

In one embodiment, it is preferred that bond 206A is applied only to the first surface of base layer 252. In one example, the bonding comprises first coating base layer 252 with amide, self-assembled-monolayers (SAMS), alkoxysilane, or thiol and then placing a solution of antibodies 208A on substrate 199 and gently rocking substrate 199 for a period of time, up to six hours. Amide refers to organic compounds that include the functional group including an acyl group, with the chemical notation C=O, linked to a nitrogen (N) atom. A SAM is an organized layer of amphiphilic molecules in which one end of the molecule, the "head group," shows a special affinity for gold, silicon, or $SiO_2$, such as that utilized in base layer 252. At the terminal end, the opposite end of the SAM from the "head group" is a functional group. In one embodiment, the first set of antibodies 208A are attached to this functional group in step 404. Lastly, a thiol is a compound that includes the functional group composed of a sulfur atom and a hydrogen atom (—SH). Being the sulfur analog of an alcohol group (—OH), this functional group is referred to either as a thiol group or a mercaptan group.

There are generally five known isotopes (types) of antibodies 208A and 208B for mammals. In FIG. 3, the Y-shape of antibodies 208A and 208B are that of monomer antibodies. There are three isotopes of monomer antibodies: IgD, IgE, and IgG, where the prefix Ig is the symbol for Immunoglobulin, and these monomer antibodies each have one unit of Ig. There is only one isotope of a dimer antibody, IgA, which has two Ig units. Finally, there is only one isotope of pentamer antibody, IgM, which has five Ig units. These antibodies are further described in copending and coassigned U.S. patent application Ser. No. 12/888,388 entitled "DETECTION OF ANALYTES VIA NANOPARTICLE-LABELED SUBSTANCES WITH ELECTROMAGNETIC READ-WRITE HEADS", which is incorporated herein by reference. The analytical process described herein may be used in human medicine, veterinarian medicine, and, as well as to other biological analyses.

In one embodiment, step 404 may include a step of rinsing substrate 199 with water or another rinsing agent to remove any antibodies 208A that are not bonded within sample trenches 180. In all rinsing steps discussed herein a surfactant may be added to the water or rinsing agent to reduce surface tension. In one example, the surfactant may include a detergent solution.

In step 406, antibodies 208A bonded within sample trench 180 are exposed to a biological sample including target antigens 210. In one example, this is accomplished by placing a blood sample or other biological sample on substrate 199. As shown in FIG. 3, the target antigens 210 bond to monomer antibodies 208A at antigen receptors 209A. The antigen receptors 209A are diagrammatically shown to be at the v-shaped end of antibodies 208A. As shown, each monomer antibody 208A has two antigen receptors 209A. Step 406 may include the repetitive rocking of substrate 199 to facilitate bonding of the target antigens 210 with antibodies 208A at antigen receptors 209A. For example the substrate is gently rocked for up to six hours. Further, step 406 may include a step of rinsing substrate 199 with water or another rinsing agent to remove antigens 210 not bonded to antibodies 208A Target antigens 210 may comprise cancer cells, viruses, or bacteria. In one embodiment, the target antigens 210 are viruses such as Human Papilloma Virus (HPV) which is known to lead to cancer. It is important to note that the antibodies 208A utilized in step 404 are specifically chosen based on the targeted antigens 210 utilized in step 406.

In step 408, a second set of antibodies 208B are bonded with nanoparticles 212. It is important to note that the first set of antibodies 208A and the second set of antibodies 208B are biologically identical, as both bond to the same target antigen 210. In one embodiment, the second set of antibodies 208B are bonded with nanoparticles 212 in parallel with steps 404 and 406. In other embodiments, the second set of antibodies 208B may be bonded with nanoparticles 212 before or after steps 404 and 406. The nanoparticles 212 include a magnetic inner core 216 and a outer shell 214. Magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality.

In one embodiment, step 408 further includes preparing the nanoparticles 212 prior to bonding the nanoparticles 212 to antibodies 208A. The preparation of nanoparticles 212 is described in FIG. 5. Magnetized nanoparticles are prone to agglomerate and form lumps. Therefore, in step 502 the magnetic inner cores 216 of nanoparticles 212 are demagnetized. In one embodiment, the magnetic inner cores 216 of nanoparticles 212 are heated above their Curie temperature to demagnetize the inner cores 216. The heated magnetic inner cores 216 are allowed to cool. The step of demagnetization keeps the inner cores 216 of nanoparticles 212 as individual particles.

In another embodiment, the step of demagnetizing the inner cores 216 of nanoparticles may be omitted. The process of manufacturing the inner cores 216 of nanoparticles may include a step of high temperature sintering. Thus, the manufacturing process of the nanoparticles 212 may demagnetize the inner cores 216. The formation of nanoparticles is taught without limitation by U.S. Pat. No. 6,962,685, entitled "Synthesis of Magnetite Nanoparticles and the Process of Forming," which is hereby incorporated by reference in its entirety.

Returning to FIG. 5, in step 504 the inner cores 216 are coated with an outer-shell 214 of nonmagnetic gold, silicon, or $SiO_2$, to create nanoparticles 212. Antibodies 208B are bonded to nanoparticles 212 via bonds 206B, such as amide, self-assembled-monolayers (SAMS), alkoxysilane, organic functional trialkoxysilane, or thiol bonds. This bonding may be accomplished by first coating nanoparticles 212 with amide, self-assembled-monolayers (SAMS), alkoxysilane, organic functional trialkoxysilane, or thiol. It is important to note that the material used for the outer shell 214 facilitates the bonding of antibody 208A within sample trench 180. The nanoparticles 212 may be placed in a solution including the second set of antibodies 208B and gently rocking this solution for a period of time. The repetitive rocking of substrate 199 facilitates bonding of the second set of antibodies 208B with the nanoparticles 212. For example, the substrate is gently rocked for up to six hours. Further, step 408 may include a step of rinsing substrate 199 with water or another rinsing agent to remove nanoparticles 212 not bonded to antibodies 208B.

In step 410, target antigens 210 are exposed to the second set of antibodies 208B bonded to nanoparticles 212. This may be done by placing a solution of nanoparticle-labeled antibodies 208B on substrate 199. As shown in FIG. 3, the target antigens 210 bond with the antigen receptors 209B of antibodies 208B. Step 410 may include the repetitive rocking of substrate 199 to facilitate bonding of the target antigens 210 with antibodies 208B at antigen receptors 209B. For example, the substrate is gently rocked for up to six hours. Further, step 410 may include a step of rinsing substrate 199 with water or another rinsing agent to remove nanoparticles 212 not bonded to target antigens 210.

In the embodiment in which substrate 199 is a Peltier substrate, the process may include an optional step of applying a DC voltage of a first polarity to the Peltier substrate. Applying a DC voltage of a first polarity heats the surface of the substrate 199 and dries the biological sample within the sample trench 180. A DC voltage of a second and opposite polarity may be applied to Peltier substrate, to cool the surface of the substrate. In an alternate embodiment, the Peltier substrate freezes the biological sample.

Returning to FIG. 1, head module 104 includes electromagnetic write-heads 106 and magneto-resistive read-sensors 108 arranged in pairs, such that each write head 106 is paired with a read sensor 108. The write head 106 may be a thin film write element. The electromagnetic write-heads 106 first write to sample trenches 180, and then the adjacent magneto-resistive read-sensors 106 immediately reads from sample trenches 180, which is referred to as a read-after-write operation. In an exemplary embodiment of the invention, the sample assembly 100 has eight sample trenches 180 corresponding to eight bits in a byte. Accordingly, in this embodiment the head module includes eight electromagnetic write-head 106 and magnetoresistive read-sensor 108 pairs. Advantageously, this is the same number of write heads and read sensors in a typical head module used in magnetic tape drive products, such as IBM® TS 1130. Therefore, in one embodiment the head module 104 may be an IBM® TS 1130 head module. It should be understood, however, any number of sample trenches 180 may be used, and the number of electromagnetic write-head 106 and magneto-resistive read-sensor 108 pairs in head module 104 may be any number. The number may be in the range from one to the number of electromagnetic write-head and magneto-resistive read-sensor pairs the head module 104. For example, in an embodiment in which there are sixteen such electromagnetic write-head and magneto-resistive read-sensor pairs, such as in a head module of an IBM® 3480 tape drive, the number of sample trenches may be sixteen. In one embodiment, the number of sample trenches 180 is an integral multiple of the number of write-head 106 and read-sensor 108 pairs. Still further, in one embodiment, the write-head 106 and the read-sensor are not separate devices. Instead a single head may perform the functions of both the e-head 106 and read-sensor 108.

As mentioned above, the sample trenches 180 may have spacing from one sample trench to the adjacent sample trench along the X-axis to match the spacing from one read sensor 108 to the adjacent read sensor 108 along the X-axis. In one embodiment the spacing between one sample trench 180 and an adjacent sample trench 180 is 166.5 microns to match the read sensor to read sensor spacing of the IBM® TS1130 tape drive.

Write-heads 106 may be any write head known in the art. In one embodiment write-heads 106 comprise miniature electromagnets, with a coil sandwiched between two poles. Read-sensors 108 may be anisotropic magneto-resistive (AMR), giant magneto-resistive (GMR), or tunnel magneto-resistive (TMR) read-sensors, or other devices with similar functionality known in the art. GMR read-sensors, which are also known as spin-valve read-sensors, typically have an internal anti-parallel pinned layer for increased sensitivity. TMR read-sensors may utilize a tunnel barrier layer to augment the GMR internal structure and to provide increased sensitivity.

As shown in FIG. 1, write-head 106 may be longer along the X-axis direction than read-sensor 108. Accordingly, the active sensing portion of read-sensor 108 is smaller than write-head 106 along the X-axis, Write-head 106 is used to magnetize nanoparticle 212 for detection by read-sensor 108 as discussed below. It is advantageous for write-head to be longer in the X-direction than read-sensor 108 because it prevents read-sensor from encountering unmagnetized nanoparticles 212, and thus, registering a false-negative detection of target antigen 210.

Head module 104 is kept in linear alignment with sample trenches 180 along the X-axis by position-error-servo (PES) read-head 192, which reads magnetically encoded servo-alignment marks 193 from servo track 194 on sample assembly 100. PES read-head 192 may be, for example, an AMR, GMR, or TMR read-sensor. In the example illustrated in FIG. 1, servo-alignment marks 193 shown are Timing Based Servo (TBS) servo-alignment marks such as those used in IBM® Linear Tape Open (LTO) tape drive products (e.g., IBM® tape product models TS1120 and TS1130). U.S. Pat. No. 6,320,719, entitled "Timing Based Servo System for Magnetic Tape Systems," is hereby incorporated by reference in its entirety for its showing of Timing Based Servo control and TBS servo-alignment marks. U.S. Pat. No. 6,282,051, entitled "Timing Based Servo System for Magnetic Tape Systems," is hereby incorporated by reference in its entirety for showing the writing of TBS servo-alignment marks.

In step 412 of FIG. 4, the process of detecting the target antigens 210 includes sweeping head module 104 with at least one magneto-resistive read sensor 108 over the sample assembly 100. In one embodiment head module 104 is moved linearly from left to right along the +Y axis relative to a stationary sample assembly. In another embodiment, the sample assembly 100 is swept linearly from right to left along the −Y axis past a stationary head module 104. If substrate 199 is of a flexible polyethylene terephthalate material, then in one embodiment, this right-to-left motion may be performed as data read-write operations in a magnetic tape drive. The head module 104 may sample a single sample trench 180, or simultaneously sample a plurality of sample trenches 180. As an alternate embodiment, head module 104 comprises a helical-scan rotary head module, and the Y-axis of the sample trench 180 is at an angle to the substrate 199. In this embodiment the sample trenches 180 are much shorter in length such that alignment of the head module 104 with sample trenches 180 may be accomplished without alignment marks 193. In one embodiment the IBM® MSS 3850 helical-scan tape drive may be utilized to detect analytes.

In one embodiment, the head module 104 comes into physical contact with the upper surface 254 of the outer layer 253 during the sweeping step of 412. Keeping the head module 104 in physical contact with the upper surface ensures that the head module 104 is kept at a known Z-axis position and assists with alignment of head module 104 with sample trenches 180. As discussed above, the outer layer 253 may comprise diamond-like-carbon, polytetrafluoroethylene, aluminum oxide, polyamides, or other low-friction materials known in the art. Accordingly, the low friction material of the outer layer assists the head module 104 to smoothly sweep the sample trenches 180 while in physical contact with the upper surface 254 of outer layer 253, such that the target antigens of the biological sample is reliably and accurately detected.

Figure 5:
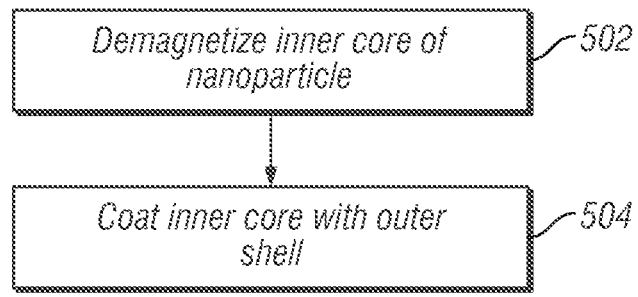
FIG. 5 is a flow chart illustrating additional steps of an analytic process in accordance with an embodiment of the invention.

As discussed with respect to step 502 in FIG. 5, in some embodiments the inner core 216 of nanoparticles are demagnetized. Accordingly, in this embodiment, as part of step 412, write-head 106 writes to nanoparticles 212 to magnetize inner cores 216 of nanoparticles. Write-head 106 writes with a constant DC magnetic polarity for the duration of the sweeping step 412, such that there are no unwritten regions of sample assembly 100. In one embodiment, write-head 106 writes with magnetically-overlapping write pulses. Further in step 412, read-sensor 108 detects the freshly magnetized inner cores 216 of nanoparticles 212, and thus detects target antigens 210. Read-sensor can detect the target antigens 210 because nanoparticles 212 are bonded to antibodies 208B, which in turn are bonded to target antigens 210.

Write head 106 magnetizes inner cores 216 of nanoparticles 212 along the Y-axis, which is the longitudinal direction of recording in the tape drive industry. Read-sensor 108 magnetically detects nanoparticles 212 along the Y-axis. As a result in step 412, the nanoparticles 212 may be magnetized by write-head 106 and then immediately and magnetically detected by read-sensor 108 during a single sweep of the sample trenches 180. As discussed above, this process is referred to as a read-after-write operation. In one embodiment, the write-head 106 and read-sensor 108 are separated by a magnetic shield (not shown) to prevent cross-talk between write-head 106 and read-sensor 108 during step 412.

Alternatively, the steps of magnetizing nanoparticles 212 and the step of detecting the nanoparticles 212 may be performed separately. For example, write head 106 magnetizes inner cores 216 of nanoparticles 212 along the Y-axis of sample assembly 100. In one embodiment, write-head 106 is then turned off. Subsequently, read-sensor 108 magnetically detects nanoparticles 212 along the Y-axis. The read module sensor 108 may be swept across sample trenches 180 along the Y-axis in both the +Y and −Y directions. Accordingly, read-sensor 108 can repeatedly check for magnetized nanoparticles 212, thus ensuring that all target antigens 210 are detected.

In an embodiment in which the number of sample trenches 180 are greater than the number of write-head 106 and read-sensor 108 pairs in head module 104, the head module 104 may scan the sample trenches 180 in a serpentine fashion. The head module 104 performs a scan in the +Y direction, as head module 104 only provides read-after-write capability in the +Y direction as shown in FIG. 1. Then, a second head module (not shown) comprising a mirror image of head module 104, conducts a read-after-write operation in the −Y direction.

The coercivity of a magnetic inner core 216 may be chosen selectively depending upon the target antigen 210 to be detected. For example, nanoparticles 212 with magnetic inner cores 216 of different coercivity values may be respectively bonded to different types of antibodies 208A and 208B to detect various types of target antigens 210 on the sample assembly 100 simultaneously. Nanoparticles 212 may have different magnetic properties associated with each antigen-antibody combination. Read-sensor 108 detects the different magnetic properties of an inner core 216 based on the materials used for that inner core 216. As discussed above, magnetic inner cores 216 may comprise hard magnetic materials with high coercivity, such as $Fe_2O_3$, $CrO_2$, and Barium Ferrite BaFe. For example, magnetic inner cores 216 may comprise iron oxide based nanoparticle materials, including M $Fe_2O_4$ (where M may be Co, Ni, Cu, Zn, Cr, Ti, Ba, or Mg) nanomaterials, and iron oxide coated nanoparticle materials or other structures with similar functionality. As a result, in step 412, read-sensor 108 may detect more than one type of target antigens 210 with a single sweep of the sample assembly 100.

Figure 6:
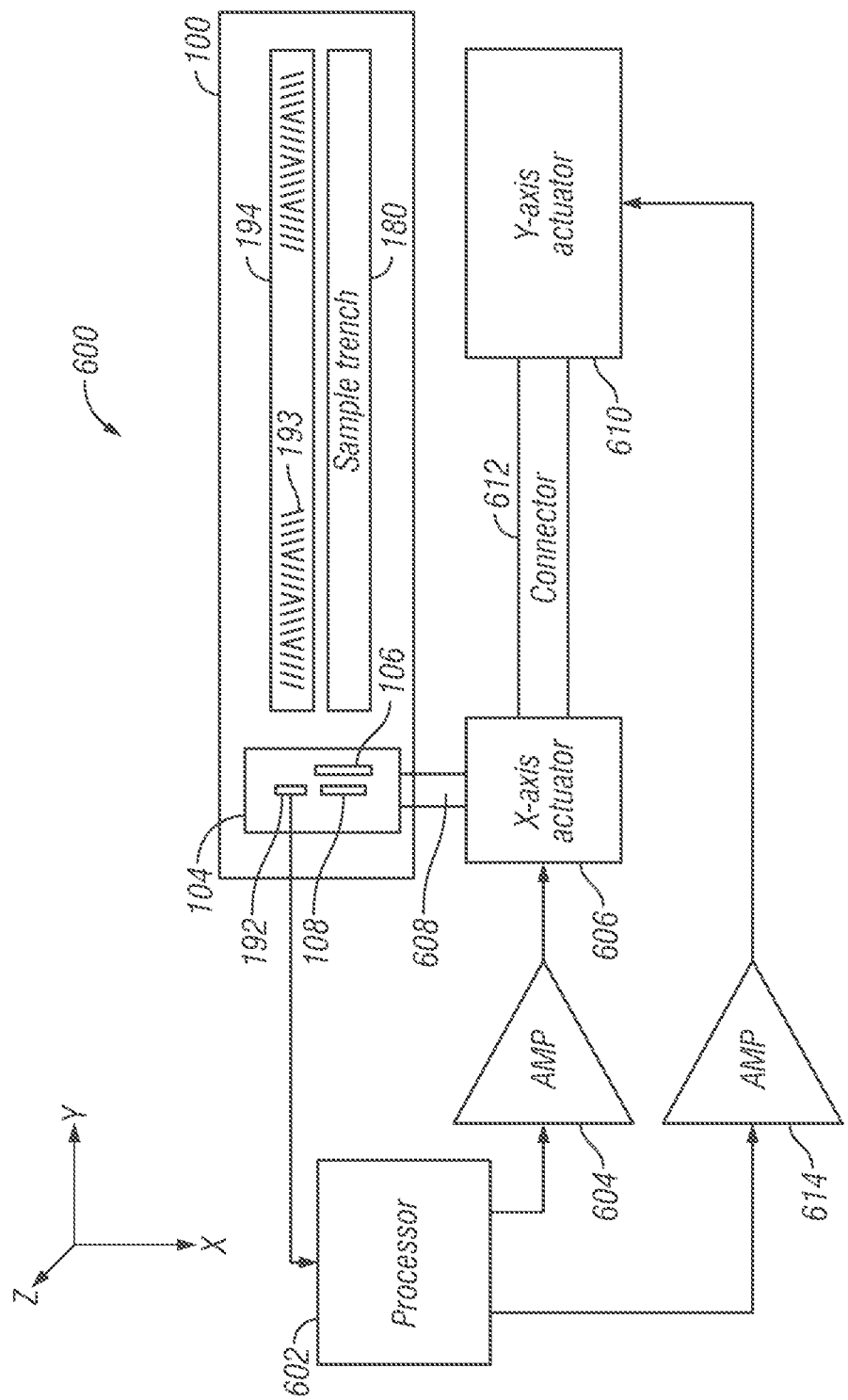
FIG. 6 illustrates control circuitry for the X-axis and Y-axis motion of the head module in an embodiment of the invention.

FIG. 6 illustrates an embodiment of a servo control system 600 for controlling the motion of head module 104 in the X-axis and Y-axis. For simplicity, FIG. 6 illustrates sample assembly 100 including a single trench 180. In addition, FIG. 6 shows a head module 104 including a single write-head 106 and read-sensor 108 pair and a PES read head 192. However, it should be understood that the sample assembly 100 may include a plurality of trenches and the head module 104 may include a plurality of write-heads 106 and read sensors 108. PES read-head 192 reads servo-alignment marks 193 in servo track 194. Processor 602 receives position-error-servo (PES) signals from PES read-head 192. Processor 602 sends a signal to power amplifier 604 to control X-axis actuator 606 based on the PES information. In turn, the X-axis actuator 606 controls the motion of head module 104 in the X-axis direction. X-axis actuator 606 is connected to head module 104 via mechanical connector 608. Accordingly, head module 104 can be positioned to center write-head 106 and read-sensor 108 on sample trenches 180 of sample assembly 100. Processor 602 also sends signals to power amplifier 614 to control Y-axis actuator 610 for conducting a scan by head module 104 across sample assembly 100. Y-axis actuator 610 is connected to X-axis actuator via mechanical connector 612, such that head module 104 can be moved along the Y-axis in a controllable manner.

Figure 7:
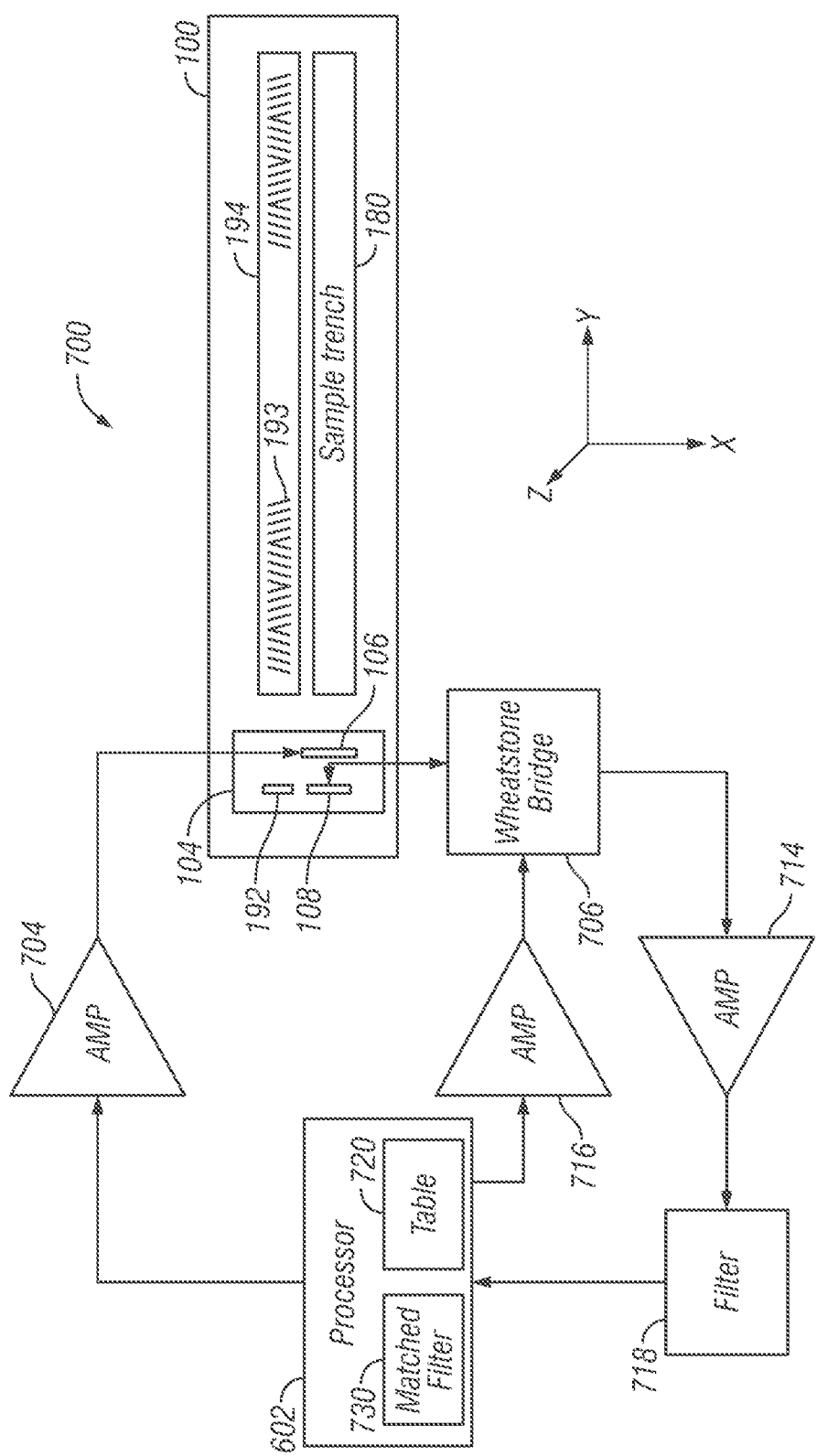
FIG. 7 illustrates read and write circuitry in an embodiment of the invention.

FIG. 7 illustrates one embodiment of a write and read circuitry 700 for use in writing to the sample trenches 180 (i.e, magnetizing nanoparticles 212) and reading from the sample trenches 180 (i.e, sensing and detecting the magnetized nanoparticles 212). For simplicity, FIG. 7 illustrates sample assembly 100 including a single trench 180. In addition, FIG. 7 shows a head module including a single write-head 106 and read-sensor 108 pair. However, it should be understood that the sample assembly 100 may include a plurality of trenches and the head module 104 may include a plurality of write-heads 106 and read sensors 108.

Processor 602 sends signals to power amplifier 704. Power amplifier provides power to write-head 106 for magnetizing nanoparticles 212. Processor 602 also sends signals to power amplifier 716. Power amplifier 716 powers Wheatstone bridge 706. In one embodiment, Wheatstone bridge includes read-sensor 108. Thus, read-sensor receives DC current from the Wheatstone bridge 706. Read-sensor 108 detects a resistance change during step 412 discussed above. The resistance change is based on the magnetic field provided by the magnetized inner cores 216 of nanoparticles 212. Wheatstone bridge 706 balances out the zero-magnetism resistance of read-sensor 108 such that only the change in resistance of read-sensor 108 is sent to amplifier 714. The amplifier 714 receives the change in resistance and sends the change in resistance to processor 602 through filter 718. Filter 718 filters out noise. In one embodiment, filter 718 filters out 60 Hz noise which is the type of noise that is pervasive in an office or laboratory setting in which processes of the invention may be performed.

Processor 602 includes a matched filter 730 and a table 720. Processor 602 determines if a nanoparticle 212 was detected, and thus, if a target antigen 210 has been detected. The change in resistance of read-sensor 108 is directly proportional to the magnetic field provided by nanoparticle 212. The change in resistance of read-sensor 108 is directly proportional to the magnetic field provided by nanoparticle 212.

As discussed above, the coercivity of a magnetic inner core 216 may be chosen selectively depending upon the target antigen 210 to be detected. For example, nanoparticles 212 with magnetic inner cores 216 of different coercivity values may be respectively bonded to different types of antibodies 208A and 208B to detect various types of target antigens 210 on the sample assembly 100 simultaneously. The identification of the target antigens 210 in the sample trenches 180 may be facilitated by a lookup table 720 in processor 602. In one embodiment, the lookup table 720 includes a list of (a) target antigens 210, (b) the antibodies 208A and 208B bonded with the target antigens 210, and (c) the coercivity of the inner cores 216 of nanoparticles 212 bonded to antibodies 208B.

In one embodiment of the invention a correlation calculation is performed by the write and read circuit of FIG. 7 to improve the detection accuracy of target antigens. The processor 602 performs correlation calculation C(y) shown in equation [1] between a detection signal profile g(y) read by read-sensor 108 when a nanoparticle 212 is detected and a matched filter 730.

$$C(y)=\int g(\eta)h)(\eta-y)d\eta \quad \text{Equation [1]}$$

In equation [1], $\eta$ is the integration variable along the Y-axis that varies as read-sensor 108 sweeps along the Y-axis. The matched filter 730 includes an impulse response h(y) of an ideal signal profile of a detected target nanoparticle 212. Since h(y) is used repetitively, it may be calculated once and stored as matched filter 730 in processor 602.

The range of correlation C(y) is between −1 and +1, where +1 represents an ideal correlation of one hundred percent (100%), and −1 indicates no correlation. The electrical waveform g(y) of each potential detection of a nanoparticle 212 by read-sensor 108 has its correlation C(y) calculated in step 412 of FIG. 4. Processor 602 then compares this correlation C(y) against a threshold correlation value Co before accepting the signal g(y) as a valid detection of a nanoparticle 212. This correlation removes spurious electrical noise from actual detections of nanoparticles, and thus reduces false-positive detections of target antigens 210.

In one embodiment, the results of the sweep of step 412 may be displayed to a physician or clinician to inform the physician or clinician of the presence (or absence) of target antigens 210 in the biological sample. The results may include items such as the target antigen(s) tested for, the types of antibodies used, a simple positive-detection or negative-detection indication for each antigen, the number of nanoparticles detected for each antigen to give an indication of the prevalence of the targeted antigen, and the number of rejected detections based on the correlation calculation.

The terms "certain embodiments", "an embodiment", "embodiment". "embodiments", "the embodiment", "the embodiments", "one or more embodiments", "some embodiments", and "one embodiment" mean one or more (but not all) embodiments unless expressly specified otherwise. The terms "including", "comprising", "having" and variations thereof mean "including but not limited to", unless expressly specified otherwise. The enumerated listing of items does not imply that any or all of the items are mutually exclusive, unless expressly specified otherwise. The terms "a", "an" and "the" mean "one or more", unless expressly specified otherwise.

Devices that are in communication with each other need not be in continuous communication with each other, unless expressly specified otherwise. In addition, devices that are in communication with each other may communicate directly or indirectly through one or more intermediaries. Additionally, a description of an embodiment with several components in communication with each other does not imply that all such components are required. On the contrary a variety of optional components are described to illustrate the wide variety of possible embodiments.

Further, although process steps, method steps, algorithms or the like may be described in a sequential order, such processes, methods and algorithms may be configured to work in alternate orders. In other words, any sequence or order of steps that may be described does not necessarily indicate a requirement that the steps be performed in that order. The steps of processes described herein may be performed in any order practical. Further, some steps may be performed simultaneously, in parallel, or concurrently.

While particular embodiments of the present invention have been shown and described, it will be obvious to those skilled in the art that, based upon the teachings herein changes and modification may be made without departing form this invention and its broader aspects and, therefore, the appended claims are to encompass within their scope all such changes and modifications as are within the true spirit and scope of this invention. Furthermore, it is to be understood that the invention is solely defined by the appended claims.

What is claimed is:

1. A method of detecting target antigens in a biological sample using a sample assembly, the method comprising:
    sweeping a head module over the sample assembly, wherein said head module includes at least one magneto-resistive read sensor configured to detect target antigens via nanoparticles operatively coupled to the target antigens positioned within at least one sample trench of the sample assembly, wherein the at least one sample trench comprises a plurality of parallel sample trenches;
    bonding a first set of antibodies to a surface of the at least one sample trench;
    sampling a plurality of servo alignment marks formed in proximity to one or more of the parallel sample trenches;
    magnetizing at least some of the nanoparticles with a write head of the head module; and
    detecting at least one particular antigen among the target antigens by detecting the nanoparticle operatively coupled to the at least one particular antigen using one or more of the at least one magneto-resistive read sensor of the head module.

2. The method as recited in claim 1, wherein the plurality of servo alignment marks comprise magnetic servo alignment marks.

3. The method as recited in claim 1, wherein the plurality of servo alignment marks comprise non-magnetic servo alignment marks.

4. The method as recited in claim 1, wherein the sampling and the magnetizing are performed simultaneously in a single sweep of the head module.

5. The method as recited in claim 1, comprising demagnetizing at least some of the nanoparticles using the write head of the head module.

* * * * *